United States Patent
Kanevsky et al.

(10) Patent No.: US 7,266,473 B1
(45) Date of Patent: Sep. 4, 2007

(54) FAST MICROARRAY EXPRESSION DATA ANALYSIS METHOD FOR NETWORK EXPLORATION

(75) Inventors: Valery Kanevsky, San Lorenzo, CA (US); Aditya Vailaya, Santa Clara, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/354,386

(22) Filed: Feb. 15, 2006

(51) Int. Cl.
*G06F 17/18* (2006.01)
(52) U.S. Cl. .................... 702/179; 702/19; 702/20; 702/22; 702/30; 382/159; 382/190; 382/224
(58) Field of Classification Search .............. 702/19, 702/20, 30, 28, 89, 22, 179; 382/224, 190, 382/159; 700/89, 28; 706/20; 707/1, 100; 704/9; 703/11
See application file for complete search history.

(56) References Cited

U.S. PATENT DOCUMENTS

| | | | | |
|---|---|---|---|---|
| 5,251,131 | A * | 10/1993 | Masand et al. | 704/9 |
| 5,479,523 | A * | 12/1995 | Gaborski et al. | 382/159 |
| 6,029,195 | A * | 2/2000 | Herz | 725/116 |
| 6,084,595 | A * | 7/2000 | Bach et al. | 345/589 |
| 6,909,970 | B2 * | 6/2005 | Kanevsky et al. | 702/19 |
| 6,963,870 | B2 * | 11/2005 | Heckerman | 707/5 |
| 6,970,790 | B2 * | 11/2005 | Kita et al. | 702/22 |
| 6,990,239 | B1 * | 1/2006 | Nelson | 382/224 |
| 2003/0112958 | A1 * | 6/2003 | Beaudoin et al. | 379/221.15 |
| 2003/0130799 | A1 * | 7/2003 | Pidgeon et al. | 702/19 |
| 2003/0217029 | A1 * | 11/2003 | Heckerman | 707/1 |
| 2004/0241696 | A1 * | 12/2004 | Peinado et al. | 435/6 |
| 2004/0265865 | A1 * | 12/2004 | Mattick et al. | 435/6 |
| 2005/0079513 | A1 * | 4/2005 | Levy et al. | 435/6 |
| 2005/0091242 | A1 * | 4/2005 | Heckerman | 707/100 |
| 2005/0209838 | A1 * | 9/2005 | Kanevsky et al. | 703/11 |
| 2005/0267852 | A1 * | 12/2005 | Heckerman | 706/20 |
| 2006/0056704 | A1 * | 3/2006 | Bachmann | 382/224 |

OTHER PUBLICATIONS

MacCarthy, T. et al., BMC Bioinformatics, "Using large-scale perturbations in gene network reconstruction", [online] http://www.biomedcentral.com/1471-2105/6/11; 8 pages.

Soinov, L., "Supervised classification for gene network reconstruction", 2003 Biochemical Society, Unravelling Nature's Networks, pp. 1497-1502.

Butilh, B., "Analysis of data from microarray experiments, the state of the art in gene network reconstruction," [online] Retrieved Apr. 14, 2005, Retrieved from: http://www-binf.bio.uu.nl/~dutilh/gene-networks/thesis.html.

(Continued)

*Primary Examiner*—Carol S. W. Tsai

(57) ABSTRACT

A method for feature selection is provided. The method includes the steps of selecting a predictor set of features, adding at least one complementary feature to the predictor set based on a quality of prediction, checking to see if all of the features of the predictor set are repeated, and if not, removing at least one feature from the predictor set. The algorithm and method repeats the steps of adding complements, checking the predictor set and removing features until the features of the predictor set are repeated. Once the features of. the predictor set are repeated the proper number of times, the algorithm and method terminate.

32 Claims, 4 Drawing Sheets

OTHER PUBLICATIONS

Somol, P. et al., "Oscillating Search Algorithms for Feature Selection", Proceedings 15th International Conference on Pattern Recognition, vol. 2, 406-409, Barcelona, Spain 2000.

Bittner, M. et al., "Molecular Classification of Cutaneous Malignant Melanoma by Gene Expression Profiling", Nature, vol. 406, Aug. 2000.

Pudil, P. et al., "Floating Search Methods in Feature Selection", Pattern Recognition Letters 15 (1994) 1119-1125, Elsevier Science B.V.

Bishop, C.M., "Neural Networks for Pattern Recognition", Clarendon Press, Oxford, 1997.

* cited by examiner

FAST MICROARRAY EXPRESSION DATA ANALYSIS METHOD FOR NETWORK EXPLORATION

CROSS-REFERENCE TO RELATED APPLICATIONS

This application is a continuation-in-part to co-pending U.S. Published Application No. 2005/0209838 entitled "FAST MICROARRAY EXPRESSION DATA ANALYSIS METHOD FOR NETWORK EXPLORATION," which is a divisional application of commonly assigned U.S. Pat. No. 6,909,970 entitled "FAST MICROARRAY EXPRESSION DATA ANALYSIS METHOD FOR NETWORK EXPLORATION," the disclosures of which are hereby incorporated herein by reference.

FIELD OF THE INVENTION

This invention relates to the field of bio-informatics and more particularly toward a method and algorithm for network exploration and reconstruction. The invention also has application to information, computer, software and data processing systems and more specifically to a method for facilitating the multiple correlation and comparisons of gene, protein and feature selection data.

BACKGROUND OF THE INVENTION

The micro-array was developed in 1995 to measure gene expression data in a massively parallel fashion. Since that time a significant increase in the amount of data per experiment has occurred (See http://www-binf.bio.uu.nl/~dutilh/gene-networks/thesis.html). In the case of gene exploration, this extensive data is important for use in assessing genes and their influence on expressed states in organisms. In particular, it is necessary to assess the function and operation of a particular gene; a gene being defined as a prescribed area on a nucleic acid molecule that is necessary for the production of a final expressed phenotype of an individual. On a more complex and broader scale, the interaction network is also of interest due to its influence in regulating higher cellular, physiological and behavioral properties. Recent attempts are being made to reconstruct the precise interaction network or its fragments based on large-scale array experiments for a condition-specific database, e.g., melanoma (Bittner et al., 2000). The critical first step in these efforts is to find the smallest subset of (predictors), within a desirable degree of precision, related to an arbitrary target. Based on such set of predictors, computed for every target of interest, it is possible to find the smallest set that can explain or predict behavior of any target in terms of expression. In the case of genes, finding the smallest set to predict a prescribed behavior could be a very complicated and arduous task given the massive amount of data that results from analyzing a complete organism's genome.

Most important to scientists is the ability to select a minimal cardinality set that can represent a whole set of expressed information. In the pattern recognition literature, this is known as feature selection or dimensionality reduction, depending on the context.

The issue at hand now is a question of mathematics and computation rather than pure biology. In particular, the specific problem at focus has been addressed from a computational standpoint. A number of algorithms can be applied from other fields and areas of study to help solve this arduous task. The specific problem at focus, from a computation standpoint, is to find the best (with respect to a given quality function) k-tuples, from a set of n features, for many values of k. One method to find the best k-tuple predictor subset is to conduct an exhaustive search through all possible k-tuples. Although this approach always leads to the best solution, it becomes intractable for even moderate values of k (the computational time grows exponentially with k).

Also important to bio-informatics will be the methods developed for pattern recognition. In the context of pattern recognition, machine learning, data mining and their applications to various subject areas, e.g., medical diagnostics, manufacturing test design, image recognition etc., a similar problem of subset selection, known as feature selection is important. A number of approaches have been proposed and designed to address these problems or issues. The approaches include and are not limited to, sequential (backward and forward) search techniques, floating search techniques and genetic algorithms, etc. However, methods based on the sequential search techniques suffer from the nesting effect, i.e., they overlook good feature sets consisting of individually poor quality features. A second method called the floating search methods (Pudil et al., 2000; Somol et al., 2000) attempt to avoid the nesting problem by successively adding the best and removing the worst subsets of features from the candidate set of features. This introduces an exponential complexity in the search when the size of a subset grows. A significant drawback of these methods is that they become slow for large dimensional data sets as is the case with biological expression data. Genetic algorithms also do not have well defined stopping criteria and, in principle, can be exponentially complex.

Most importantly, the above methods and algorithms are intended to be applied in the field of array data processing to enable computationally efficient searches for the smallest subset of features that predict a target's expression levels within a given level of confidence or accuracy.

It would, therefore, be desirable to develop a method and algorithm that determines "good" solution sets with high probability in linear time, with respect to total number of features in a predictor set. For this reason, "sequential forward selection" (SFS) (Bishop, 1997; Pudil et al., 2000; Somol & Pudil, 2000) was developed to add the best (the one that leads to the largest improvement in the value of the quality function) new feature, at each successive stage of the algorithm, to the current set of features until the needed number of features is reached. It follows from construction that SFS suffers from the nesting problem and always overlooks better solutions sets whose features are of mediocre or poor quality. This is one of the shortcomings addressed by the present invention. While "sequential floating forward selection" (SFFS) also addresses the nesting problem, it maintains exponential time complexity for large data sets. The second shortcoming that this invention addresses is the exponential time complexity to find "good" solutions. The proposed method and invention finds a "good" solution set with high probability in linear time with respect to number of predictors. One of the floating search algorithms, called "oscillating search", (Somol & Pudil, 2000) can also find approximate solutions in linear time. However, the present invention and method guarantees an equal or better quality solution while maintaining the linear time complexity. In addition, the same generic method or algorithm can be used not only for gene network reconstruction, but also can be applied to protein data, feature selection for classification and other biological data that is very large and complex to organize and analyze.

BRIEF SUMMARY OF THE INVENTION

The invention is a method for determining a predictor set of features associated with a target. The method comprises the steps of selecting a predictor set of features, adding a complement to the predictor set based on a quality of prediction, checking to see if all of the features of the predictor set are repeated and then removing one feature from the predictor set. The algorithm and method repeats the steps of adding, checking and removing features until the features of the predictor set are repeated. If the features of the predictor set are repeated, the algorithm and method terminate.

More specifically, the invention is a method for probabilistically determining a subset of features of size k that are closely related to a given target in terms of a selected quality function. The method of the invention operates by allowing a user to select a target of choice and the size (k) of the predictor set. Once a target has been selected, the method starts by selecting an arbitrary (ordered) subset of features of size k−1 and iteratively adds and removes single features (in order) from the selected subset. This process is iterated until a subset of features of size k is found whose quality of prediction of the target can no longer be improved by the process of deletion followed by addition of a feature. The algorithm terminates at this stage. In each iteration, the comparisons are based on a quality function that determines a quality of prediction associated between the predictors and the target. The method of invention can easily be extended to probabilistically determine the smallest (in size) subset of features that are closely related to a given target within an a priori set tolerance level in terms of a selected quality function. The method then takes as input a given target (user selected) and iteratively applies the method of invention for subsets of size 1, 2, 3, . . . , k, etc., until a predictor set that is closely related to the target expression, within the a priori set threshold, is found. The method can also be used for classification of experiments. The method in this case defines a target in terms of a vector of numbers representing the class of experiments under consideration. The method can then be used to identify a subset of features which can classify the data.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION

Figure 1:
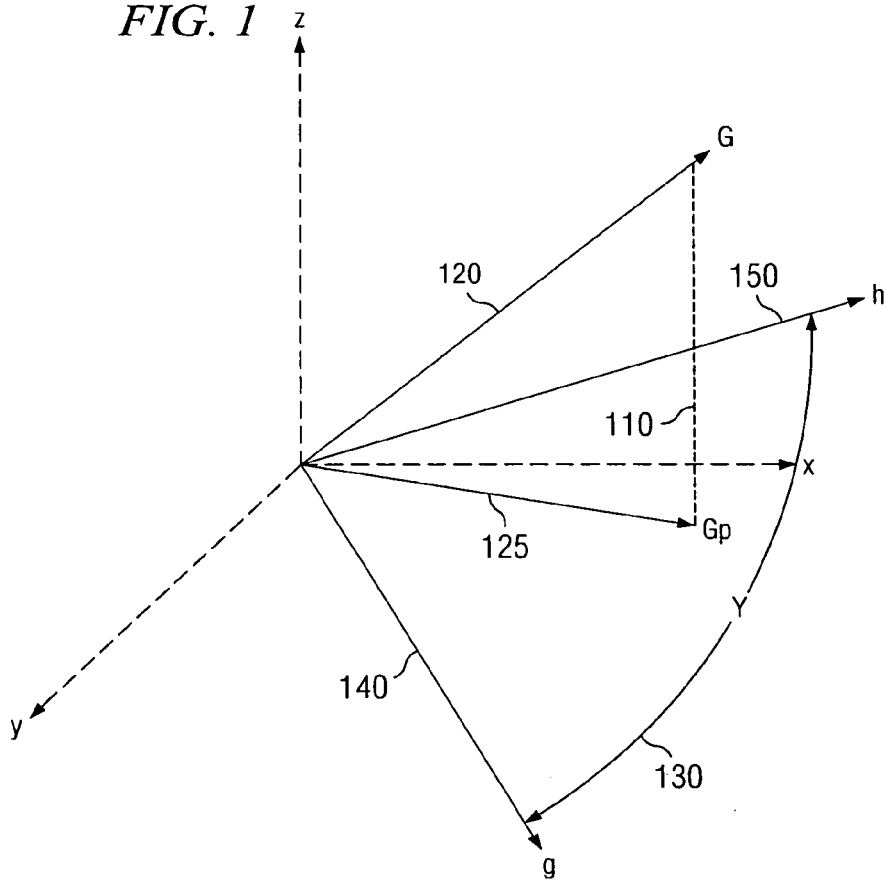
FIG. 1 illustrates a schematic view of the present invention in vector format showing the target and the predictors.

Before describing the present invention in detail, it is to be understood that this invention is not limited to specific compositions, process steps, or equipment, as such may vary. It is also to be understood that the terminology used herein is for the purpose of describing particular embodiments only, and is not intended to be limiting. The invention has broad based use and application in a variety of fields including most importantly the fields of chemistry, biochemistry, computer science and biology.

It must be noted that, as used in this specification and the appended claims, the singular forms "a", "an" and "the" include plural referents unless the context clearly dictates otherwise. Thus, for example, reference to "an attractor" includes more than one attractor, reference to "a predictor" includes a plurality of predictors and the like.

In describing and claiming the present invention, the following terminology will be used in accordance with the definitions set out below.

The term "feature" shall be broad enough to encompass the full range of possible definitions, including fields such as target recognition, image processing, feature extraction, data exploitation, and biological definitions, such as expression levels or biological data of a defined gene, protein, or other biological function or component under consideration and over a prescribed number of experiments.

The term "network reconstruction" shall mean the process, apparatus, steps and algorithms used in determining associated and/or non-associated pathways in a data set. In particular, it shall mean the relationships or pathways between two or more predictor sets.

The term "target" shall be broad enough to encompass the full range of possible definitions, including fields such as target recognition, image processing, feature extraction, data exploitation, and biological definitions, such as proteins, genes, immunological information, feature selection for classification, and other complex biological and chemical data and/or components that may be defined over a number of experiments. The term has particular meaning to chemical and biochemical data that is extensive, complex and difficult to analyze. For instance, in the case of genes it shall mean the expression levels over the number of experiments of a selected gene of interest.

The term "predictor set" or "predictor set of features" shall be broad enough to encompass the full range of possible definitions, including fields such as target recognition, image processing, feature extraction, data exploitation, and biological definitions, such as proteins, genes, immunological information, feature selection for classification, and other complex biological and chemical data and/or components for a given size k, that are used to compute or predict an associated quality or characteristic of a target. For instance, in the case of gene vectors of a given size, k, it is used to compute or predict an expression level of a target gene vector.

The term "predictor(s)" is used for a feature that is part of a predictor set.

The term "prediction" is a vector, computed by using a linear/non-linear function of features in the predictor set (although, we describe the proposed invention in terms of linear prediction function, the method is not limited to the same; it can be extended to other prediction functions such as non-linear, etc.).

The term "quality" or "quality of prediction" shall herein mean the distance between the prediction and the target. The smaller the distance between the predictor and the target the better (or higher) the quality of prediction. Geometrically, for k=2, quality is the distance between the target and the plane formed by the two features in the predictor set. It should be noted that this definition of the quality function should not be interpreted as limiting and any other computable function may be used.

The term "distance" shall not be limited to Euclidean distance measures, but shall be broad enough to include weighted distances for non-linear coordinate systems.

An "attractor" or "solution set" shall mean a set of a given size k of features such that the quality of prediction can not be improved by replacing one feature in the set. In other words, in the case of gene data, a set of genes S is an attractor if the quality of its prediction of the target gene, G, cannot be improved by substituting only one gene in this set (in some sense an attractor is a local minima). It should be noted that the best solution is always an attractor.

The term "complement" shall mean a feature (when looking for a predictor set size of k features it is defined as follows: a feature g is called a complement to a given set of k−1 features if no other feature, along with this given set of k−1 features, can form a higher quality set of k predictors). In the case k=2, gene g* is called a complement to feature g if the "quality" $Q(.,.)$ of the couple $(g,g^*)$ is no worse than that of any couple $(g,h)$; $Q(g,g^*) \leq Q(g,h)$ for any h.

The term "k-tuples" shall mean a group of size k. For instance, if k=2, then we call them a "couple". In addition, if k=3 we call them a "triplet". This is an abbreviated term to show the relationship between group size and designated pairings.

The term "good solution" shall mean a set of predictors having a given size with high enough quality, which corresponds to a distance that is smaller than some maximum limit.

The term "M-dimensional space" shall mean a variety of orientations and positions in space (i.e., M=1 . . . 1000, arbitrary and large).

The term "data cube" shall mean a multi-dimensional matrix that can be indexed by referencing any of its dimensions or combinations of dimensions.

When a search for the best (in quality) group of individuals is conducted, the term "nesting" or "nesting effect" shall mean procedures that are based on the assumption that a good in quality group consists of good in quality subgroups, overlooking solutions made up of mediocre or poor (in quality) individuals.

The array is a significant new technology aimed at providing a top down picture of the intimate processes of an organism. Whether an array is implemented using photolithography and silicon-based fabrication, capillary printing heads on a glass slide, or ink-jet technology, it allows for quantification of large amounts of data simultaneously. Few years have passed since the first micro-array based biological results were published and it already seems unthinkable to tackle the complexities of the workings of the cell without these devices. However, there remains unsolved image processing as well as computational and mathematical difficulties associated with the extraction and validation of data for micro-array assays.

Network reconstruction's main function is to discover the existence and determine the association of multiple dependencies between biological or transcriptional data that leads to the identification of possible associated pathways. There are a number of potential motivations for constructing algorithms, and computer software for network reconstruction. For instance, diagnostics and the diagnostic industry can use these techniques and tools for application in disease identification. Other potential valuable applications include treatment selection and outcome prediction. In addition, the derived information can be further applied to aid in drug development and areas of feature selection for classification.

The references cited in this application are incorporated in this application by reference. However, cited references are not admitted to be prior art to this application.

Feature Selection in Pattern Recognition

The problem of network reconstruction, based on micro-array data, can be reduced to finding dependencies within a subset of features in terms of their expression levels. One meaningful option to address this problem is to find a set of best k predictors for any target of interest.

In the context of pattern recognition, machine learning, data mining and their applications to various subject areas, e.g., medical diagnostics, manufacturing test design, image recognition, etc., a similar problem of subset selection, known as feature selection is faced. We have discussed this related work in feature selection and the advantages of the proposed method over these works in the Section "Background of the Invention". We concentrate here on the method of invention.

The method described below is somewhat similar to what are called the "sequential forward selection" (SFS) and "sequential floating forward selection" (SFFS) methods. SFS adds the "best" (i.e. the one that leads to the largest improvement in the value of the quality function) new feature, at each successive stage of the algorithm, to the current set of features until the needed number of features is reached. In particular, SFS suffers from the nesting problem and always overlooks better solution sets whose features are of mediocre or poor quality. This is one of the shortcomings addressed by this invention. While SFFS also addresses the nesting problem, it maintains exponential time complexity for large data sets. The second shortcoming that this invention addresses is the exponential time complexity to find "good" solutions. The method finds a "good" solution set in linear (with respect to k) time with high probability. One of the floating search algorithms, called "oscillating search", can also find an approximate solution in linear time. However, the method guarantees an equal or better quality solution while maintaining the linear time complexity. The methods and algorithm of the present invention may be used and employed in a variety of systems that receive or export large volumes of data or information. In particular, the algorithm and/or method have potential application with computer and/or computer software. The algorithm may be used, employed or supplied with other similar hardware, software, or systems that are well known in the art.

Referring now to FIG. 1, the first step in a network reconstruction entails the search for strong linear dependencies among associated data, i.e.:

$$G \sim F(g, h \ldots) \quad (1)$$

where G 120 is the target of interest and g 140, h 150 are predictors. The function F can be linear or non-linear. In this application, we investigate only the linear case:

$$F = \alpha * g + \beta * h \quad (2)$$

where α and β are constants.

The quality of a linear prediction of a target G 120, associated with a set of features, g 140, h 150, is given by the quality function Q 110:

$$Q(G; g, h) = \min_{\alpha, \beta} \frac{\sum_{i=1}^{M}(G_i - \alpha g_i - \beta h_i)^2}{\sum_{i=1}^{M} G_i^2} \quad (3)$$

FIG. 1 shows a representation of the g 140 and h 150 vectors in 3 dimensional space. Each vector is defined by three components x, y and z, which are the expression levels of a feature over a set of three experiments. G, h and g are three arbitrary vectors in 3-dimensional space and the figure is for illustration purposes only and should not be interpreted as limiting the scope of the invention in any way. In addition, the use of x, y, and z coordinate systems and the described planes should not in any way be interpreted as limiting the broad scope of the invention. The quality of a given pair g 140, h 150, as predictors of G 120, is the distance between the plane formed by these two vectors and target vector G 120 (See FIG. 1 for more details). $G^P$ 125 is defined as the projection of G 120 on the plane 130 formed by g 140 and h 150.

Greedy Subset Search Algorithm (GSSA)

Figure 2:
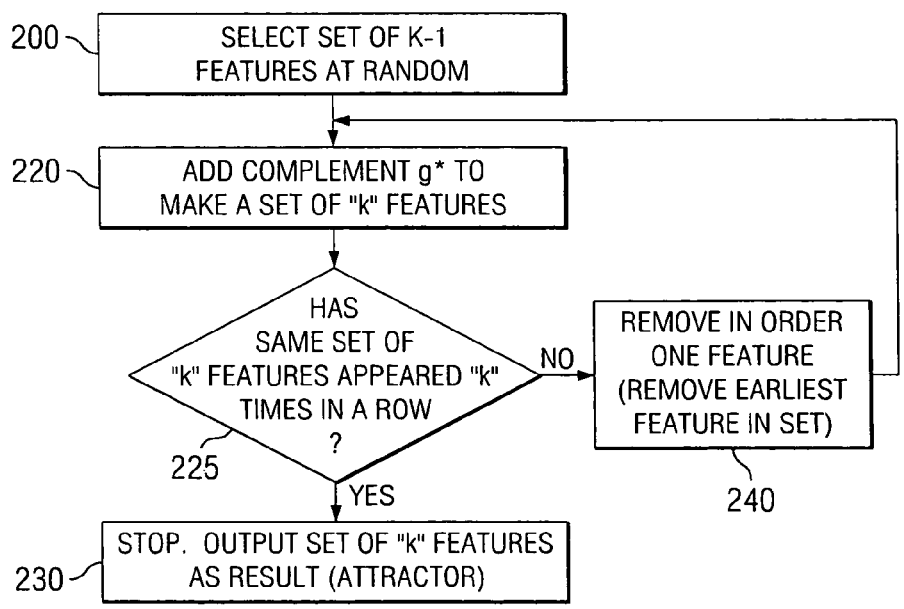
FIG. 2 shows a block diagram of the method of the invention.
Figure 3:
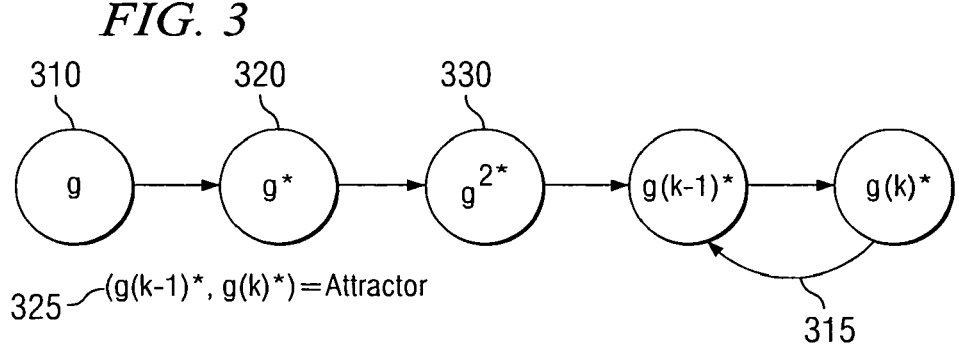
FIG. 3 shows how the GSSA algorithm makes comparisons of data.

Referring now to FIGS. 1-3, the algorithm starts with an ordered, randomly selected subset of k−1 features. Next, this subset is complemented by one feature, which along with selected features forms the best possible (in quality) subset of k features. Number k is assigned to this feature. The feature number one is removed from the set and numbering of remaining genes: 2, . . . , k is reduced by one to become 1, . . . k−1. This subset of k−1 features is an input to the next iteration of the loop 315 (See FIG. 3).

Iterations continue until the quality of a set of k predictors can not be further improved by replacing any one feature in the set 325 (See FIG. 3).

Method Outline: The Algorithm

Let $S = \{g_1 \ldots, g_n\}$ be expression levels of N features observed over the course of M experiments and let G 120 be an arbitrary target with expression levels over the same group of experiments. In this way, all features are represented by vectors in M-dimensional space. G 120 may or may not belong to S 200 (not shown in diagrams). In what follows, we will refer to every element of S 200 as a feature.

General Definition:

We say that a subset, $s \subset S$ 200, of features predicts the target G 120, with accuracy δ if the distance between the linear subspace generated by s and G 120 equals δ.

The Euclidean distance has been selected as a measure of proximity. Given this, and the linearity of the subspace, the definition above is simply stated as follows: the Least Squares distance between the subset s and the target G 120 equals:

$$\delta = \min \frac{\left\| G - \sum_{g_j \in S} \alpha_j g_j \right\|}{\|G\|} \quad (4)$$

where min is taken over all sets of k real numbers $\alpha_j$ and ‖ ‖ represents the norm in M-dimensional space. The algorithm, in its current implementation, doesn't take advantage of the specificity of the distance definition and, therefore, can be applied to any search problem of described nature with an arbitrary proximity measure. The value of δ will be referred to as the quality Q(s) 110 of a set of predictors s.

FIG. 2 shows a block diagram of the method of the present invention and how the algorithm works with the predictor and target data for a given size k of the predictor set. A target 120 of interest is first selected (not shown in the block diagram, but shown in FIG. 1). The method then selects an ordered subset of features of size k−1. If k=2, then the method randomly selects a feature, say g 140 (shown as reference number 200 in the block diagram). To this subset the method now adds the complement feature, i.e., to form the best subset of size k (in terms of quality of prediction) that has the initially chosen subset of k−1 features. The quality of prediction of this subset of k features is then noted (shown as reference 220 in the block diagram). Next, the algorithm performs a checking step to see if the same set of k features have appeared k times in a row (shown as reference number 225). If the answer is "yes" the algorithm stops and outputs the set of k features as the result. This is called an attractor (shown as reference numeral 230 in the diagram). If the answer is "no" the algorithm removes in order one feature from the predictor set (shown as 240 in the block diagram). The algorithm continues and repeats the steps of adding a complement, checking the predictor set and removing a feature until the same set of k features has appeared k times in a row.

This process (of deleting a feature and adding another feature) may be repeated many times until a subset is reached whose quality of prediction can not be improved by deleting and then adding a single feature. This subset of size k (k=2 here) is referred to as an "attractor" 230 (shown generally as 230 is the block diagram of FIG. 2). The method then terminates and outputs the "attractor" as the best (in terms of quality of prediction of the target expression) solution set of size k (k=2 here). The process can be modified, to probabilistically select the smallest (in size) subset of predictors that is closely related to the target in terms of the quality of prediction, as follows. The method starts with an initial predictor set size of k=2 as described above. If the "attractor" set that the method outputs does not lie within the acceptable threshold of quality of prediction, the predictor set size is incremented by one, i.e., k=3. The algorithm uses the "attractor" of the previous stage (k=2) as the starting subset of size k−1 at this stage. The method is iteratively applied with increasing value of k, until an "attractor" is found that is related to the target within the a priori set threshold of quality of prediction.

Referring now to FIG. 3, the definition of "attractor" and "complement" will now be clarified. FIG. 3 shows how a feature g 310 is first complemented by g* 320. g* 320 is a "complement" to g 310 implies that the set consisting of features g 310 and g* 320 has the best quality of prediction of all sets of size k=2 having feature g 310. Feature g 310 is then removed and a new "complement" feature $g^{(2)}*$ 330 is added to g* 320 and so on until the final predictor set ($g^{(k-1)}*$, $g^{(k)}*$) 325 is found, such that the "complement" of $g^{(k)}*$ is the same as $g^{(k-1)}*$ (comparisons are shown by reference numeral 315). At this stage no deletion or addition of a single feature can improve the quality of prediction. Such a predictor set that can no longer be improved is called an "attractor" or solution set.

Definition of Complement(s):

Referring to FIG. 3, feature g* 320 is called a complement to a set, i.e. g*=(s)* if the quality of the set s∪g* is better or equal to the quality of s∪g for any choice of g 310, i.e., $$Q(s \cup g^*) \leq Q(s \cup g) \qquad (5)$$

Definition of Attractor(s):

A set of features s is called an attractor (with respect to the complement) if (s')*∪s'=s for any subset s' of s that contains all but one element of s, i.e., one can not improve the quality of a set of predictors s by substituting only one feature (See FIG. 3).

The Problem and Algorithm:

For a given number k=2, 3 . . . , a set of n features s, and a target G 120, find the best quality subset of features s of size k. To solve the problem an algorithm has been designed. The main loop of this algorithm is defined as a cycle for one seed set s'. For a given k, the solution starts with a seed set s' of the size k−1.

One cycle of the main loop:
   Let s [i] represent the $i^{th}$ element in s.
   Set index=0;
   Randomly generate or otherwise select seed set s' of size k−1;
   Set current best attractor, s=ϕ(empty set);
   Repeat unconditionally
   {
   Find the complement g* of s', i.e., g*=(s')*;
     /* there is always assumed seniority order in s, i.e., later complements have greater index, e.g., g*=s[k]*/
   If (s'∪g*=s) then
   {
     s=s'∪g*;
     index=index+1;
     if (index=k) then break out of the loop;
   }
   else
     /* find a new set of better quality than s */
   {
     index=1;
     s=s'∪g*;
   }
   Form new seed set s' as s without its first element s[1];
   }
   Print set s as the predictor set;

The number of cycles in the main loop can be controlled by (i) the quality of a current set of predictors; (ii) total computational time; and (iii) direct constraint on the number of cycles itself. From a practical point of view, the above methods are suitable for parallel processing. Since each loop begins with a random subset of data, all that is necessary for the computation is to allow the method to generate these random subsets, and compare with previously computed best subsets. Therefore, different initiations of the algorithm can be distributed across processors, as long as different random seed subsets are used in each loop and the computed best subsets are appropriately compared.

The algorithm above has been provided so that one of ordinary skill in the art can design and write code from it. Java software was used to code the algorithm in experimental runs. Experiments and data were run on a Personal Computer (PC) with a Windows NT (operating system). The system had 512 MB RAM and a 800 MHz CPU (processor). One of ordinary skill in the art needs to use a programming language to make a software prototype of the algorithm. He/she needs to have a computer that has the software coding environment loaded. No special hardware requirements are necessary to run this algorithm. The larger the size of RAM and the more processing power (parallel processors would be even better), the better. Methods in exhaustive searches are also well known in the art and need not be described here in detail.

Algorithm Performance:

It can be shown that one cycle of the main loop always terminates and the predictor set it terminates at is an "attractor". It is obvious that the best (in quality) set of genes must be an "attractor" as well. Therefore, given everything equal, the algorithm's performance depends on the number of "attractors" or possible solution sets; the less the number of "attractors" the more likely the loop terminates at the optimum.

If π is the probability that one cycle of the main loop terminates at the best "attractor", then the probability that after P iterations of the main loop, the best "attractor" will be visited at least once is:

$$1-(1-\pi)^P \qquad (6)$$

It has been observed in numerous computations using both generated and real data that as the number of "attractors" goes down when the number of experiments (dimensions of space) goes up.

In other words, as more independent experiments are conducted, the reliability of the data improves. Since the number of "attractors" reduces with increasing number of experiments, the probability of finding the best in quality "attractor," i.e. optimal solution set, using the GSSA algorithm, increases.

The probability, π, of finding the optimal "attractor", however, goes down with the increase in the number of genes, N, and the increase in the predictor set size, k. This is intuitive, since the number of possible "attractors" will increase with an increase in the number of genes or the size of the predictor set.

The figures described and illustrated below were plotted using the software Matlab for PC. The PC was running Windows NT. Other methods well know in the art can be used also to plot the data. Matlab was used because of its simplicity in requiring (x and y pairs) of data for plotting. These and other plotting methods are well known in the art. However, the described applications and plots should in no way be limiting of the broad scope of the invention. The program can be coded to run on other computers and different software may be used to plot the results. FIGS. 4-8 show plots of data from a series of runs on the GSSA algorithm. The plots show the application of the algorithm and method to gene reconstruction.

Figure 4:
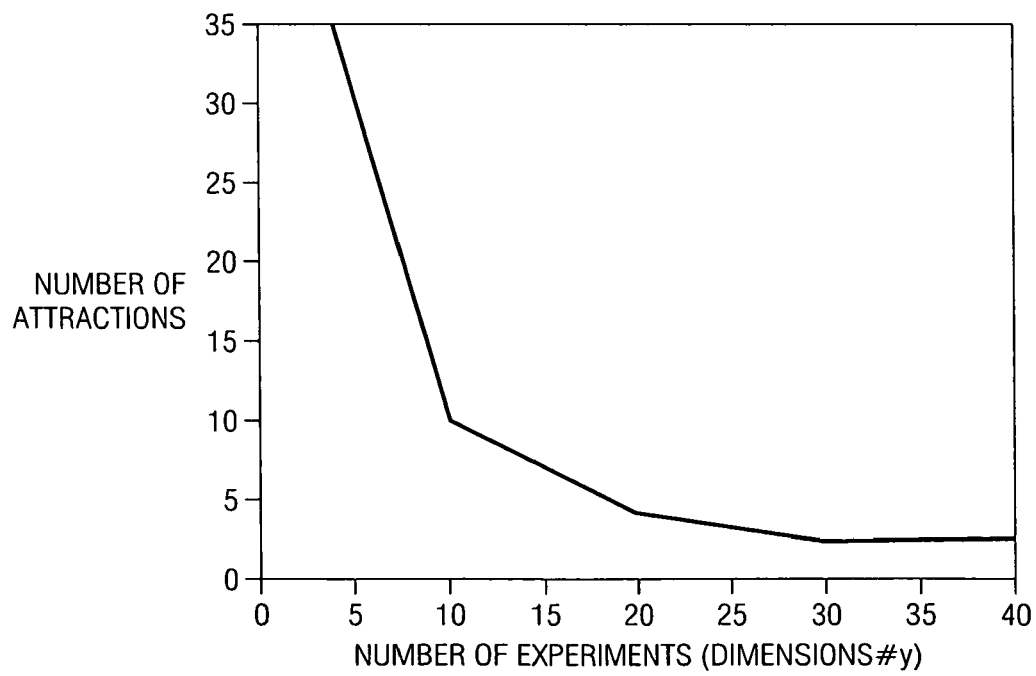
FIG. 4 shows a simulated plot of the number of attractors v. the number of experiments.

FIG. 4 shows a plot of (Nattr) plotted against Nexp. The plot shows the number of attractors of size 2 (i.e., k=2) as dimensionality of the data increases. Each gene is represented as a vector in m-dimensions. These m-dimensions are the m experiments that were conducted on all the genes in the set S. This simulation consists of expression of 200 genes in 40 experiments. Thus, size of the set S is 200, and m=40. The graph shows how the number of attractors of size 2 (k=2) decreases as more experimental values are considered. It shows that as we use more experiments, we have less number of attractors and hence, a better chance at reaching the best solution in a few random runs of the GSSA algorithm. The use of the algorithm provides a special blessing of dimensionality toward a final solution. As has been described above, the number of "attractors" can actually be controlled by the number of experiments. In addition, the number of "attractors" can be estimated a priori (proof beyond the scope of the invention). Existence of multiple "attractors" for a given data set may be evidence of insufficient amount of experiments to draw confident conclusions regarding the nature of dependencies among genes. It also suggests a specific number of additional experiments to be performed to substantiate the conclusion.

Another point to be noted is that there is a tradeoff between the number of genes replaced at each step of the algorithm and the quality of "attractor". For instance, the computational time increases exponentially as the number of replaced genes goes up, but the algorithm may stop at a better quality "attractor". However, one gene replacement algorithms converge to a high "quality" attractor with high probability, given a sufficient number of experiments.

Figure 5:
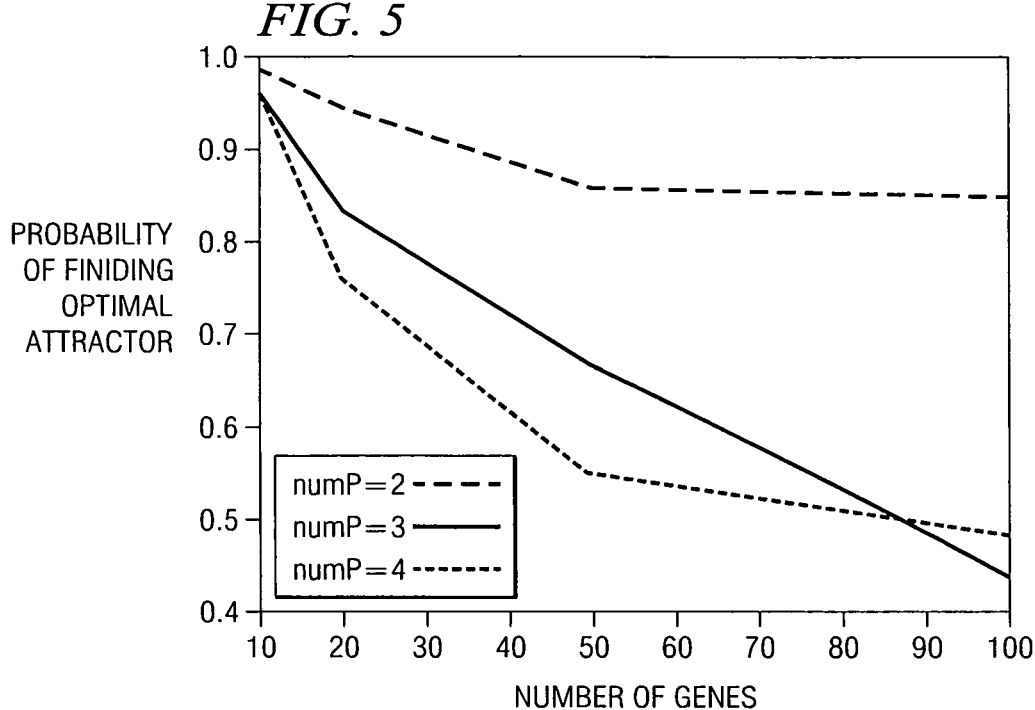
FIG. 5 shows a simulated plot of the probability of finding an optimal attractor v. number of genes.

FIG. 5 shows a simulated plot of the probability of finding the optimal predictor set in a single run of the approximate algorithm. As can be determined from the diagram, as the number of genes increases the probability in most cases decreases in finding the actual predictor set. FIG. 5. shows the probability to find the best solution (best attractor of size k=numP in the graph) from a set of N (x-axis of the graph) genes in one run of GSSA. One run of GSSA means, starting with one random seed and running the GSSA algorithm until an attractor is found. The dimensionality of the data here (the number of experiments or m was fixed and was 38). Three plots are shown in this figure. The top plot shows the results for k=numP=2. The middle plot shows results for k=numP=3 and the bottom plot shows results for k=numP=4. The top plot and other plots are similar. The top plot (k=numP=2) shows that the probability of finding the best solution drops as we increase the number of genes. This is because there exist more attractors as the number of genes increases. Now the difference in the three plots also shows that as we keep the number of genes fixed (take a fixed value on the x-axis), but increase the value of k (i.e., increase k from 2 to 4), we see that the probability of finding the best solution also decreases (and this too is because the number of attractors increases as the size of k increases). If $\pi$ is the probability of reaching the best solution in one run of GSSA, then the probability that it reaches the best solution in p trials is $1-(1-\pi)^p$ which can be brought close to 1 if we increase p.

Figure 6:
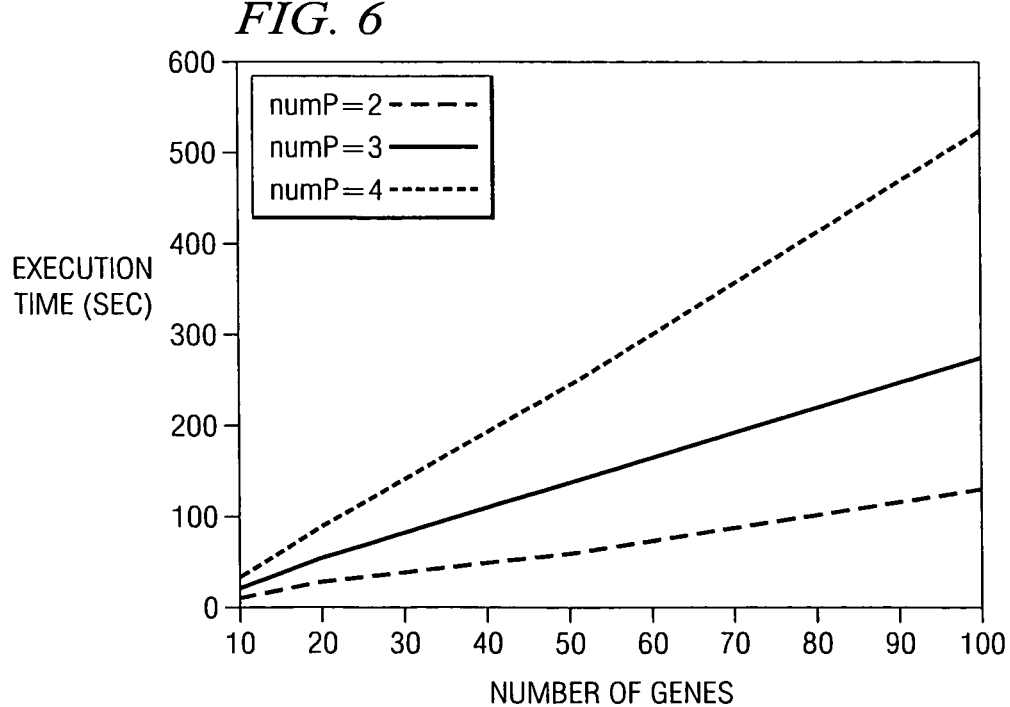
FIG. 6 shows a simulated plot of the execution time v. number of genes.

FIG. 6 shows a simulated plot that demonstrates the computational complexity of the approximate algorithm increases linearly as opposed to an exponential increase using an exhaustive search. The diagram shows a plot of execution time vs. number of genes. It becomes evident that as the number of genes increases, the execution time increases in a linear fashion. The fact that the execution times (as the number of genes increases) lie on a line indicates the linear nature of the algorithm. FIG. 6. shows the execution time of running GSSA 50 times versus the total number of genes. We take 50 random start seeds and run the GSSA until it reaches an attractor for each of the 50 instances. Then we select as the best answer, the best result of the 50. The size of set S of genes from which to choose the predictors is increased in the experiment. We see that the execution time increases linearly. The three plots show for three cases (k=numP=2, 3, 4). The exhaustive search that finds the best solution has an exponential increase in time.

Figure 7:
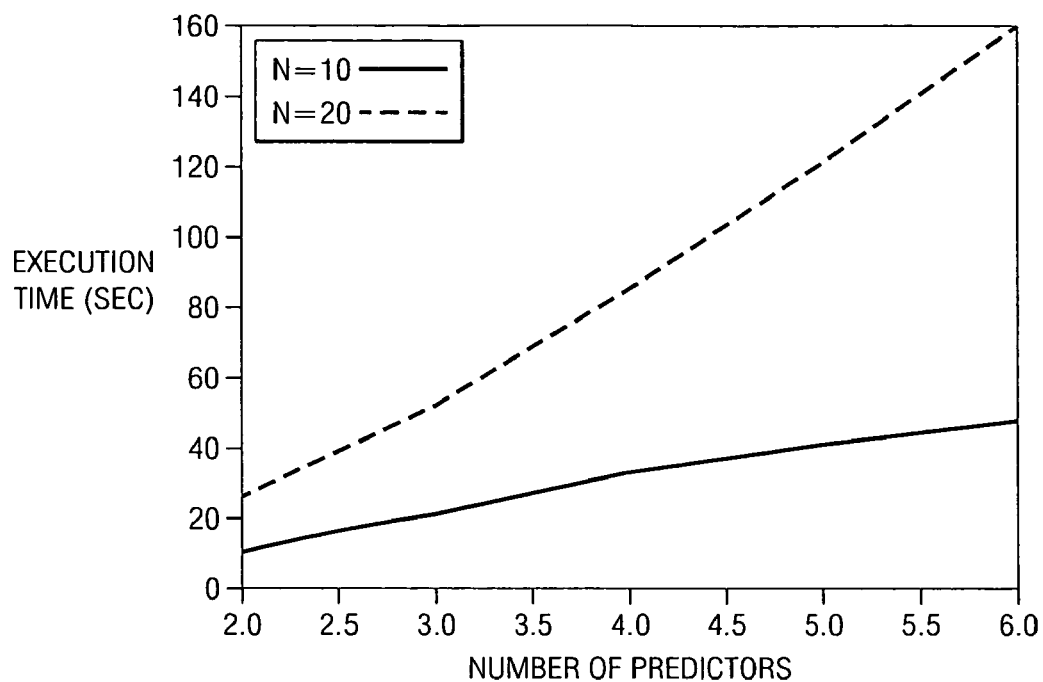
FIG. 7 shows a simulated plot of the execution time v. number of predictors.

FIG. 7 shows a simulated plot of the execution time of the algorithm as a function of the number of predictors. The results of the plot indicate that as the predictor set size increases, the execution time also increases, but in a linear fashion. In other words, the execution time does not increase at the same exponential rate as exhaustive search when there is an increase in the number of predictors. This is very important for calculations necessary in the gene network reconstruction. What may take years to complete (due to the exponential nature of exhaustive search) may now be completed in a matter of few minutes. FIG. 7. keeps number of genes fixed (S is fixed) and varies k=numP and plots the execution time for 50 runs of the GSSA algorithm. The execution times can be divided by 50 to yield time to run for a single run of GSSA (take one random seed and run GSSA until you reach an attractor). Again the execution time increases linearly with increase in k. Two plots are shown for size of S=10, and 20. Note that the execution times for FIG. 6. and FIG. 7. are for the algorithm implemented in Java and running on a PC running Windows NT with a CPU of 800 MHZ and 256 MB RAM (memory).

Figure 8:
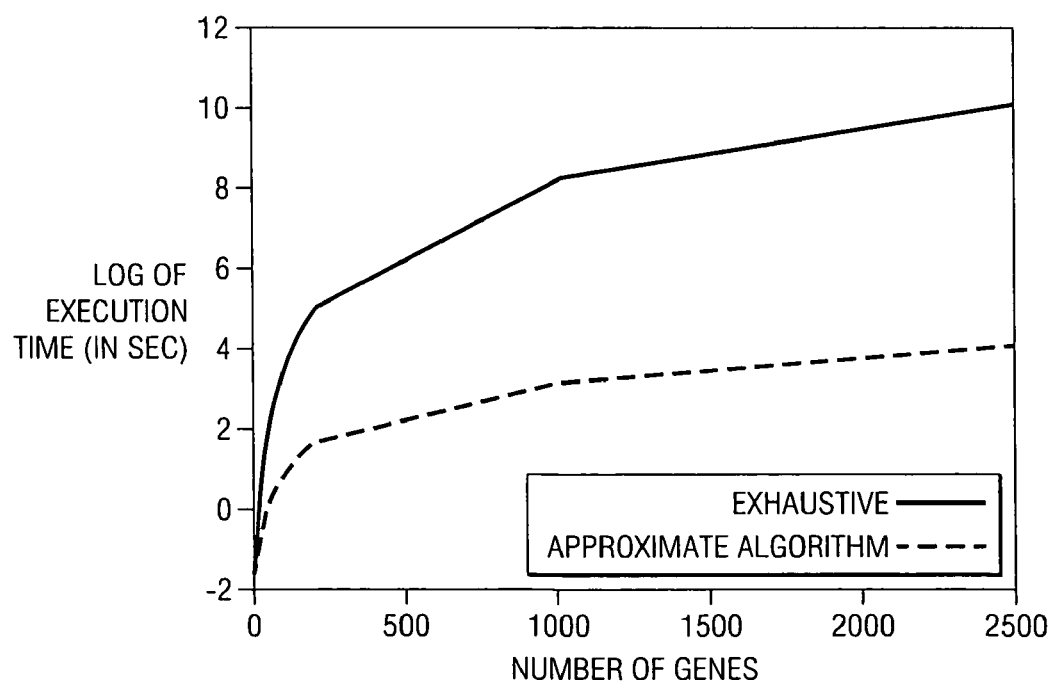
FIG. 8 shows a simulated plot of the log of the execution time v. number of genes.

FIG. 8 shows a plot of the log of execution time against number of genes. The trend in this plot is similar to the trends presented in the previous plots. The plot clearly shows the novelty and power of the present algorithm in finding "good" solutions that may be effective in the gene network reconstruction problem. FIG. 8. also shows the difference between execution times for the GSSA algorithm and the exhaustive search. The number of genes (size of S) is varied and the execution times are shown as log (to the base e-natural logarithm). Here, we show time for only 1 run of GSSA (as against 50 runs of the algorithm in FIG. 6. and 7.). This shows that this algorithm is extremely fast as compared to exhaustive search methods that are well known in the art.

Further Applications of the Invention

The method of invention can easily be extended to probabilistically determine the smallest (in size) subset of features that are closely related to a given target within an a priori set tolerance level in terms of a selected quality function. The method then takes as input a given target (user selected) and iteratively applies the method of invention for subsets of size 1, 2, 3, . . . , k, etc., until a predictor set that is closely related to the target expression, within the a priori set threshold, is found.

Embodiments of the invention are designed to return a good solution set, which is defined as a local maximum with sufficiently high quality. The good solution set that is returned may not necessarily be the global optimum, or best possible feature set, but it is a set which cannot be improved by replacing any single feature. Multiple instances of the invention may be started using different seed sets. Based on the number of starting points, the size of the data set, and the number of different solution sets from the various trials, it is possible to assess the probability that the highest possible quality "attractor," or optimal solution set, has been found. It is obvious to see that, given an appropriate starting seed set, certain embodiments of the invention will find the particular optimal solution set.

The method of the invention can also be used for classification. According to one embodiment, a method defines a target in terms of a vector of numbers representing the class of the experiments under consideration. Such a method can be used to identify a subset of features that can predict the class of the experiment within the given quality of prediction. As an example (though not limiting the use of the invention), we can consider a micro-array data for say, leukemia. The data includes gene expression results for different tissues (a tissue sample represents one experiment) representing various types of leukemia. If we assign a number for each type of leukemia (say, 0, 1, 2, etc.), then we can define a target over all the experiments by the vector of numbers representing the type of leukemia represented by the tissues. We can now use the method of one embodiment of the invention to identify a "good" subset of genes that can predict the target vector (and hence the type of tissues). Hence, these genes can form a diagnostic set of genes whose expression values are used to discriminate between the various types of leukemia.

Embodiments of the invention may be used to find a good solution set for a specified size, k, or else find the size k and accompanying solution set for a specified minimum quality threshold. For this latter use, the value of k is varied until the minimum quality threshold is satisfied by a solution set of size k.

While various examples are provided herein for applying embodiments of the present invention to biological data sets and/or network reconstruction, application of the present invention is not limited to these fields. Rather, embodiments of the present invention may be applied to classification problems in general, in which object are assigned to certain classes based on measurements of various parameters or features. For example, during the quality assurance (QA) step of a manufacturing process, a seam, joint, solder connection or other connection may need to be checked. It can be examined from multiple aspects, and different properties can be measured, such as length, weight, area and other descriptive features. Various subsets of features may be useful for different classification problems. Embodiments of the invention can perform feature selection, wherein it is applied for determining a subset of features that is useful for a certain classification problem.

In the example of the QA for a solder joint, the goal is to classify the joint as either good or bad. During the QA process, there may be several images taken of the joint using either X-ray or some other optical scanning method. Various features may be extracted, such as the size, length, thickness, weight or color. These features are the total set of features. However, a smaller subset of K features, out of the total set of features, is desired that can classify the joint as either good or bad.

In addition to quality analysis for manufacturing, other potential applications include economics, image and data processing, target recognition, behavior-modeling and machine vision, as examples. For an economic application, an embodiment of the present invention can assist with determining which economic indicators are useful for forecasts or diagnosing events. An embodiment of the above-described algorithm may be applied in determining a relatively small group of stocks or information sources out of a much larger group of stocks or information sources that may serve as a predictor of investment opportunities. For example, it could select a few stocks or stock metrics that reliably predict the performance of any investment opportunity from a large segment of the stock market down to one particular stock. The investment questions could have different time-frames, and be as broad as determining the performance of the entire stock market or narrowly focused on a single investment opportunity.

For example, it may be desirable to find a relatively small set of stocks that predicts the performance of the S&P 500 Index. Various stock features can be used in the total set of features in addition to just price, such as price-to-earning ratio, trading volume and others. The total set of features can include not only the prices of the candidate stocks, but the other market and trading information as well. The set of K features is then found from the total set.

An example in the field of target recognition could be the selection of the smallest set of features needed for fingerprint or computerized photo identification. For example, a smaller set of features may be desired that still results in the correct identification of a person with acceptable reliability. Behavior-modeling for marketing or credit card fraud detection could also benefit. For fraud detection, a set of training data should be available that is already classified as either fraudulent or not, along with a total set of observed behaviors. The observed behaviors could include time of day, type of purchase, and location of the transaction. An embodiment of the invention can then find a smaller set of K behaviors out of the total set of observed behaviors to use for classifying a credit card transaction as fraudulent or not.

Various modifications to the embodiments of the invention described above are, of course, possible. Accordingly, the present invention is not limited to the particular embodiments described in detail above.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of feature selection comprising:
   (a) selecting a weighted subset of (k–x) features associated with a target, either individually or in combination, k being a number greater than 1 and x being a number greater than 0 and less than k;
   (b) adding x complementary features to said subset to form a predictor set of k features;
   (c) selecting a counting threshold, T, that is greater than or equal to k;
   (d) checking to see if all of said k features of said predictor set have been repeated T times in a row;

(e) if determined in step (d) that all of said features of said predictor set have not been repeated T times in a row, removing at least x features from said predictor set and returning to step (b); and (f) as a result of determining in step (d) that all of said features of said predictor set have been repeated T times in a row, then selecting such predictor set as a best predictor set of k features for predicting said target.

2. The method of claim 1 further comprising:

(g) determining whether the best predictor set of k features satisfies a predetermined quality of prediction threshold, then incrementing the value of k.

3. The method of claim 2 further comprising:

(h) if determined in step (g) that the best predictor set of k features does not satisfy a predetermined quality of prediction threshold, then incrementing the value of k; and (h) repeating steps (a)-(g) for the new value of k.

4. The method of claim 1 wherein T is equal to $$\frac{k!}{(k-x)!x!}.$$

5. The method of claim 1 wherein the predictor set and target are vectors in M-dimensional space.

6. The method of claim 1 wherein said k features of the predictor set are ordered; and wherein said x features that are removed from said predictor set in step (e) are the first x features in the ordered predictor set.

7. The method of claim 6 wherein said x features that are added in step (b) are added to the end of the list.

8. The method of claim 1 wherein said selecting of (k-x) features in step (a) uses at least some degree of randomness.

9. The method of claim 1 further comprising:
using said formed predictor set of k features to determine whether said target is present in a sample.

10. The method of claim 1 wherein the weights of the features include both positive and negative real numbers.

11. The method of claim 1 wherein combinations of features includes all Boolean logic operations.

12. The method of claim 1 wherein the data are economic data.

13. The method of claim 1 wherein the data are manufacturing data.

14. The method of claim 1 wherein the data are patterns extracted from a data cube.

15. The method of claim 14 wherein the data cube is an image.

16. A computer readable medium having computer executable instructions for feature selection that when executed cause a computer to perform the steps of:

(a) selecting a weighted subset of (k-x) features associated with a target, either individually or in combination, k being a number greater than 1 and x being a number greater than 0 and less than k;

(b) adding x complementary features to said subset to form a predictor set of k features;

(c) means for selecting a counting threshold, T, that is greater than or equal to k;

(d) checking to see if all of said k features of said predictor set have been repeated T times in a row;

(e) if determined in step (d) that all of said features of said predictor set have not been repeated T times in a row, removing at least x features from said predictor set and returning to step (b); and (f) as a result of determining in step (d) that all of said features of said predictor set have been repeated T times in a row, then selecting such predictor set as a best predictor set of k features for predicting said target.

17. The computer readable medium of claim 16 further comprising:

(g) determining whether the best predictor set of k features satisfies a predetermined quality of prediction threshold, then incrementing the value of k.

18. The computer readable medium of claim 17 further comprising:

(h) if determined in step (g) that the best predictor set of k features does not satisfy a predetermined quality of prediction threshold, then incrementing the value of k; and (h) repeating steps (a)-(g) for the new value of k.

19. The computer readable medium of claim 16 wherein T is equal to $$\frac{k!}{(k-x)!x!}.$$

20. The computer readable medium of claim 16 wherein the predictor set and target are vectors in M-dimensional space.

21. The computer readable medium of claim 16 wherein said k features of the predictor set are ordered; and wherein said x features that are removed from said predictor set in step (e) are the first x features in the ordered predictor set.

22. The computer readable medium of claim 21 wherein said x features that are added in step (b) are added to the end of the list.

23. The computer readable medium of claim 16 wherein said selecting of (k-x) features in step (a) uses at least some degree of randomness.

24. The computer readable medium of claim 16 further comprising:
using said formed predictor set of k features to determine whether said target is present in a sample.

25. The computer readable medium of claim 16 wherein the weights of the features include both positive and negative real numbers.

26. The computer readable medium of claim 16 wherein the data are economic data.

27. The computer readable medium of claim 16 wherein the data are manufacturing data.

28. The computer readable medium of claim 16 wherein the data are patterns extracted from a data cube.

29. The computer readable medium of claim 28 wherein the data cube is an image.

30. A method comprising the steps of:

(a) selecting a subset of (k-1) features associated with a target;

(b) adding at least one complement feature to said subset to form a predictor set of k features;

(c) selecting a counting threshold, T, that is greater than or equal to k;

(d) checking to see if all of said features of said predictor set have been repeated k times in a row;

(e) if determined in step (d) that all of said features of said predictor set have not been repeated k times in a row, removing at least one feature from said predictor set and returning to step (b); and (f) as a result of determining in step (d) that all of said features of said predictor set have been repeated k times in a row, then selecting such predictor set as a best predictor set of k features for predicting said target.

31. The method of claim 30 further comprising:
using the determined best predictor set of k features for predicting the presence of said target.

32. The method of claim 30 wherein said target comprises one selected from the group consisting of:
biological target, reconstructed network, economic target, quality assurance target, image recognition target, fingerprint recognition target, pattern recognition target, and signal detection target.

* * * * *